(12) United States Patent
Miesel

(10) Patent No.: US 8,083,730 B2
(45) Date of Patent: Dec. 27, 2011

(54) IMPLANTABLE THERAPEUTIC SUBSTANCE DELIVERY DEVICE WITH RESERVOIR VOLUME SENSOR

(75) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1611 days.

(21) Appl. No.: 11/413,302

(22) Filed: Apr. 28, 2006

(65) Prior Publication Data

US 2007/0255259 A1  Nov. 1, 2007

(51) Int. Cl.
*A61K 9/22* (2006.01)
*A61M 37/00* (2006.01)
*A61M 1/00* (2006.01)
*A61M 31/00* (2006.01)
*G01F 17/00* (2006.01)

(52) U.S. Cl. ............ 604/891.1; 604/131; 604/132; 604/151; 604/153; 604/288.01; 604/288.04; 604/500; 604/502; 604/890.1; 604/93.01; 73/149

(58) Field of Classification Search ........... 604/131, 604/140, 141, 132, 891.1, 288.02, 153, 288.01, 604/288.03, 288.04, 502, 65, 151, 500, 890.1, 604/93.01; 73/149
See application file for complete search history.

(56) References Cited

U.S. PATENT DOCUMENTS

| | | | | |
|---|---|---|---|---|
| 4,386,716 A | * | 6/1983 | Buck | 222/37 |
| 4,772,263 A | * | 9/1988 | Dorman et al. | 604/132 |
| 5,090,234 A | * | 2/1992 | Maresca et al. | 73/49.1 |
| 5,507,737 A | * | 4/1996 | Palmskog | 604/891.1 |
| 5,974,873 A | * | 11/1999 | Nelson | 73/149 |
| 6,210,368 B1 | | 4/2001 | Rogers | |
| 6,286,377 B1 | * | 9/2001 | Benke et al. | 73/865.9 |
| 6,305,381 B1 | | 10/2001 | Weijand et al. | |
| 6,669,909 B2 | * | 12/2003 | Shvets et al. | 422/502 |
| 6,755,814 B2 | * | 6/2004 | Wieland et al. | 604/891.1 |
| 2003/0090263 A1 | * | 5/2003 | Heinrich et al. | 324/207.15 |
| 2004/0087894 A1 | | 5/2004 | Flaherty | |
| 2005/0075624 A1 | | 4/2005 | Miesel | |
| 2005/0187515 A1 | | 8/2005 | Varrichio et al. | |
| 2006/0089619 A1 | | 4/2006 | Ginggen | |
| 2007/0255260 A1 | * | 11/2007 | Haase | 604/891.1 |

OTHER PUBLICATIONS

A PCT Search Report mailed Apr. 4, 2007 (12 pgs.).

* cited by examiner

*Primary Examiner* — Kevin C Sirmons
*Assistant Examiner* — Shefali Patel
(74) *Attorney, Agent, or Firm* — Dicke, Billig & Czaja, PLLC

(57) ABSTRACT

An implantable medical device for delivering a therapeutic substance including a housing and a volume sensor assembly. The housing includes a stationary wall and maintains a reservoir containing the therapeutic substance and including a base wall movable relative to the stationary wall such that reservoir volume is a function of a spacing between the base wall and the stationary wall. The volume sensor assembly includes a cap, a shaft, a target, and circuitry. The cap defines a passage extending from an open end, and is mounted to the stationary wall such that the open end is open relative to a stationary wall inner face. The shaft has a first end attached to the base wall and a second end maintaining the target otherwise movably arranged within the passage. The circuitry generates information indicative of a longitudinal position of the target relative to the cap, and thus of the reservoir volume.

33 Claims, 7 Drawing Sheets ated the implantable delivery device, and related methods of operating the implantable delivery device.

IMPLANTABLE THERAPEUTIC SUBSTANCE DELIVERY DEVICE WITH RESERVOIR VOLUME SENSOR

BACKGROUND OF THE INVENTION

The present invention relates to implantable medical devices for delivering a liquid therapeutic substance to a delivery site within a patient. More particularly, it relates to systems and methods for estimating or indicating a residual volume of therapeutic media contained within a reservoir of an implantable delivery device, and related methods of operating the implantable delivery device.

A variety of implantable medical devices are available for treating patients. For example, implantable therapeutic substance delivery devices are typically used to deliver infusion media or therapeutic substance (such as medication) to a patient at a regulated dosage. The implantable therapeutic substance delivery device (sometimes referred to as a drug pump or medicament pump) is implanted by a clinician into a patient at a location appropriate for the therapy. Typically, an infusion catheter is connected to an outlet of the device, and is implanted/positioned to infuse the therapeutic substance at the desired therapy site so as to treat a condition such as pain, spasticity, cancer, neurodegenerative diseases, trauma, diabetes, and other medical conditions. In addition to the implantable delivery device and the catheter, available intrathecal therapeutic substance delivery systems conventionally include an external programmer that facilitates wireless communication between the delivery device and the clinician. Regardless, the delivery device includes a housing maintaining a reservoir within which the therapeutic substance is contained, along with a pump and/or metering mechanism (and related control circuitry, if necessary) that operates to control flow of the therapeutic substance from the reservoir.

The drug reservoir can assume a variety of configurations, but normally is adapted to impart a positive pressure onto the contained therapeutic substance to better ensure continuous dispensement so long as the reservoir is at least partially filled. For example, one well-accepted design incorporates a bellows assembly as part of the reservoir, and forms a propellant chamber opposite the reservoir. A propellant (e.g., inert gas) within the propellant chamber creates a positive pressure on the bellows assembly that, in turn, positively acts upon the contained infusion media. With this technique, then, as therapeutic substance is withdrawn from the reservoir, the bellows assembly contracts via the external force created by the propellant. One such implantable therapeutic substance delivery device is the SynchroMed® EL implantable drug pump available from Medtronic, Inc., of Minneapolis, Minn. A number of different designs can also be employed that may or may not include a bellows arrangement.

Regardless of exact design, over time, the therapeutic substance in the reservoir becomes depleted and it is necessary to refill the device with a new supply of therapeutic substance. In order to avoid the need for surgery to access and refill the device, it is desirable to have the ability to percutaneously refill the drug reservoir. This is commonly done by providing the delivery device with a fill port assembly that establishes fluid access to the drug reservoir from an exterior of the device. In this regard, a resilient, resealable septum is provided with the fill port assembly, and is accessible by percutaneously inserting a hypodermic needle through the skin and then the septum. Once the septum has been pierced, the hypodermic needle is fluidly connected to the drug reservoir to permit refilling.

While efforts have been made to optimize the refill port design, for example in terms of ease of identification and needle insertion, clinicians may still experience difficulties in determining whether refilling of the reservoir is needed. That is to say, while available devices are capable of ensuring consistent refilling via percutaneous interface, the clinician may not have a complete understanding of how much therapeutic substance is currently contained within the device. While it is possible to track the volume of therapeutic substance dispensed over time (either manually or automatically) and compare the tracked dispensed volume with the reservoir volume when initially filled, a clinician may further desire a confirmation of the actual contained volume. In light of the hermetic, metallic barrier commonly associated with the reservoir along with the importance of preventing contact between the contained therapeutic substance and materials that are otherwise incompatible with the media, no viable device for measuring therapeutic substance reservoir volume has heretofore been available.

In light of the above, a need exists for an implantable therapeutic substance delivery device that is capable of generating information indicative of a current volume of the drug reservoir or a residual volume of the contained therapeutic substance.

SUMMARY OF THE INVENTION

Aspects in accordance with the principles of the present invention relate to an implantable medical device for delivering liquid therapeutic substance to a delivery site within a patient. The device includes a housing and a volume sensor assembly. The housing includes a stationary wall and maintains a drug reservoir. The stationary wall has an inner face and an outer face. The reservoir defines an internal region for containing the therapeutic substance and includes an inlet, an outlet, and a base wall. The base wall is movable relative to the stationary wall. Further, a volume of the internal region is determined as a function of distance between the base wall and the stationary wall. The volume sensor assembly is adapted to generate information indicative of a current volume of the internal region and includes a cap, a shaft, a target, and circuitry. The cap defines an internal passage extending from an open end to a closed end. Further, the cap is mounted to the stationary wall such that the open end of the passage is open relative to the inner face. The shaft has a first end and a second end, with the first end being attached to the base wall opposite the cap. The target is maintained by the second end of the shaft and is movably arranged within the passage. Finally, the circuitry is associated with the cap and is adapted to generate information indicative of a longitudinal position of the target relative to a dimension of the cap. With this in mind, the longitudinal position of the target relative to the dimension of the cap is representative of the volume of the internal region. In some embodiments, the target is a ferromagnetic material and the circuitry includes a plurality of wire coils wound about an exterior of the cap, with inductance information generated by the wires being indicative of a position of the target.

Other aspects in accordance with principles of the present invention relate to a method of operating an implantable medical device adapted to deliver a liquid therapeutic substance, otherwise contained within a drug reservoir thereof, to a delivery site within a patient following implantation. The method includes operating a volume sensor assembly associated with the drug chamber to obtain target position information. In this regard, the volume sensor assembly includes a cap, a shaft, a target, and circuitry. The cap defines an internal passage extending from an open end to a closed end, with the cap being mounted to a stationary wall associated with the reservoir such that the open end of the passage is open relative to a base wall associated with the drug chamber. The shaft has a first end attached to the base wall opposite the cap. The target is maintained by a second end of the shaft and is movably arranged within the passage. Finally, the circuitry is associated with the cap and is adapted to generate information indicative of a longitudinal position of the target relative to the cap, with this information constituting the obtained target position information. The obtained target position information is processed to generate information indicative of a current volume of the reservoir. Finally, a determination is made as to whether or not to add therapeutic substance to the reservoir based upon reference to the generated current volume information. In some embodiments, the current volume information represents a relative difference between the current volume of therapeutic substance contained within the reservoir and a volume of the drug reservoir when full. In other embodiments, the method further includes operating an enunciation device to generate a series of audible tones as a function of the current volume information.

Yet other aspects in accordance with principles of the present invention relate to an implantable medical device for delivering a therapeutic substance to a delivery site within a patient. The device includes a housing and volume sensing means. The housing includes a stationary wall and maintains a drug reservoir defining an internal region for containing the therapeutic substance. The reservoir further includes an inlet, an outlet, and a base wall that is movable relative to the stationary wall. In this regard, a volume of the internal region is a function of a distance between the base wall and the stationary wall. The volume sensing means is provided for generating information indicative of a current volume of the internal region. In this regard, the volume sensing means includes position indicating means for generating information indicative of a relative position of the base wall relative to the stationary wall. In some embodiments, the volume sensing means include target means connected to the base wall and slidably disposed within a receiving means, and circuitry means for generating information indicative of a longitudinal position of the target means relative to the receiving means.

DETAILED DESCRIPTION OF THE INVENTION

Figure 1A:
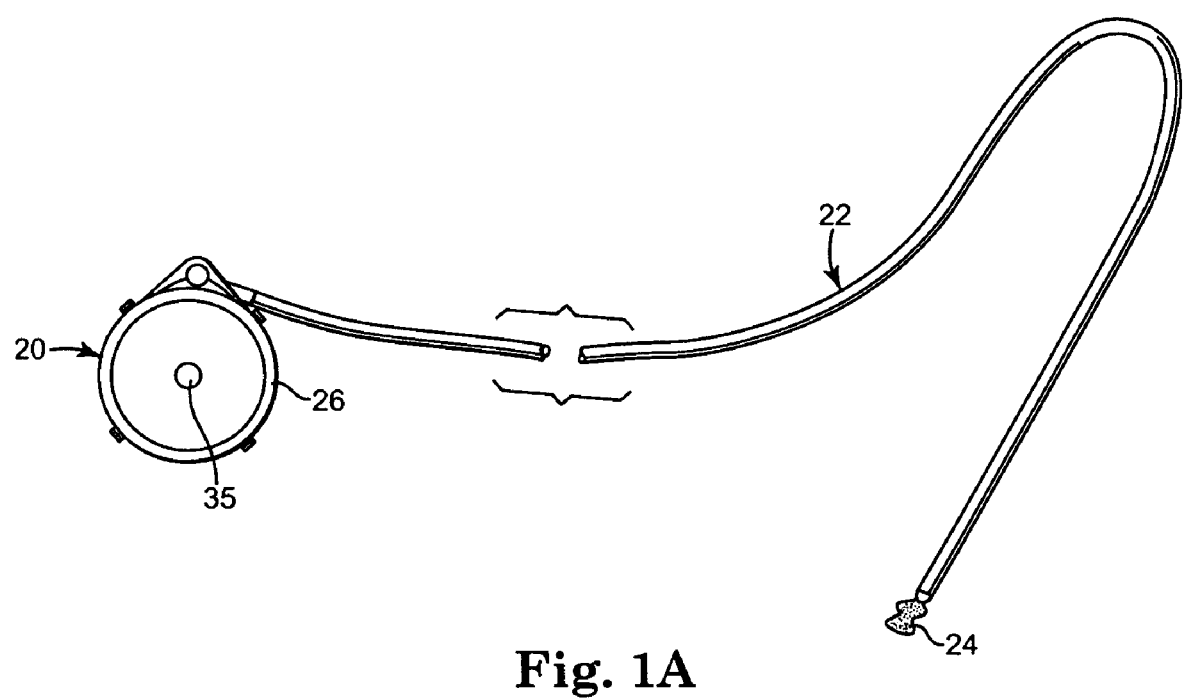
FIG. 1A is a top plan view of an implantable therapeutic substance delivery device in accordance with principles of the present invention along with a delivery catheter.
Figure 1B:
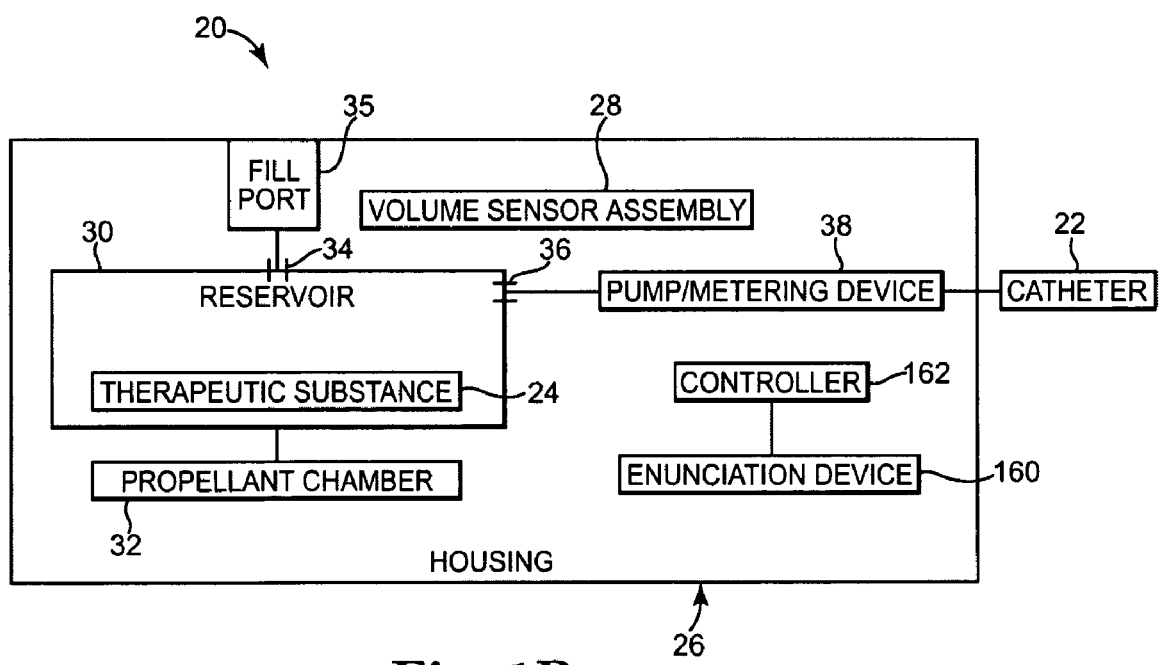
FIG. 1B is a block diagram of the implantable therapeutic substance delivery device of FIG. 1A.

One embodiment of an implantable therapeutic substance delivery device 20 in accordance with principles of the present invention is shown in FIGS. 1A and 1B, along with an implantable intrathecal catheter 22. In general terms, the implantable therapeutic substance delivery device 20, also known as a drug pump, can assume a variety of forms, and can be provided as part of an intrathecal infusion system that further includes an external programmer (not shown), for example as provided with a SynchroMed® EL Infusion System available from Medtronic, Inc., of Minneapolis, Minn. Regardless, the implantable therapeutic substance delivery device 20 operates to infuse a therapeutic substance 24 (drawn generally in FIG. 1A) into a patient via the catheter 22. The therapeutic substance 24 can be any infusion agent, product, or substance intended to have a therapeutic effect such as pharmaceutical compositions, genetic materials, biologics, and others (e.g., insulin, saline solution, fluoroscopy agents, etc.).

With the above in mind, and with specific reference to FIG. 1B, the implantable therapeutic substance delivery device 20 includes a housing 26 and a volume sensor assembly 28. Details on each of the various components is provided below. In general terms, however, the housing 26 defines a reservoir 30 that contains the therapeutic substance 24 and defines a variable volume as described below. In some embodiments, a propellant chamber 32 is also provided, formed against the reservoir 30 and serving to place a constant positive pressure on to the reservoir 30. The therapeutic substance 24 is filled into the reservoir 30 via an inlet 34 (e.g., a refill port 35 including a septum), and releases the therapeutic substance 24 via an outlet 36. In this regard, the implantable therapeutic substance delivery device 20 can include a pump mechanism and/or metering device 38 in some embodiments that dictates the amount or volume of the therapeutic substance 24 drawn from the reservoir 30. To this end, the pump mechanism 38 can assume a wide variety of forms as is known in the art. Regardless, the outlet 36 is fluidly connected to the catheter 22 for subsequent delivery of a desired amount of the therapeutic substance 24 from the outlet 36 to the patient (not shown). The volume sensor assembly 28 is maintained by the housing 26 and is adapted to sense information indicative of a volume of the reservoir 30, and thus indicative of a residual volume of the therapeutic substance 24 contained within the reservoir 30.

The implantable therapeutic substance delivery device 20 can incorporate a number of features not otherwise illustrated in FIGS. 1A and 1B. For example, a power source (not shown) can be provided as part of the pump mechanism 38 along with an electronics module or controller, such as with a positive or peristaltic configuration. Alternatively, the implantable therapeutic substance delivery device 20 can assume a passive infusion configuration whereby the propellant chamber 32 serves as a pump drive, with flow from the reservoir outlet 36 being passively controlled, in some embodiments, through capillary tubing (not shown) or similar structure(s) (akin, for example, to the IsoMed™ Implantable Constant-Flow Infusion Pump available from Medtronic, Inc., of Minneapolis, Minn.). Further, other programmable module(s) (not shown) can be included. Thus, the implantable therapeutic substance delivery device 20 is not limited to the configuration represented in FIGS. 1A and 1B.

Figure 2:
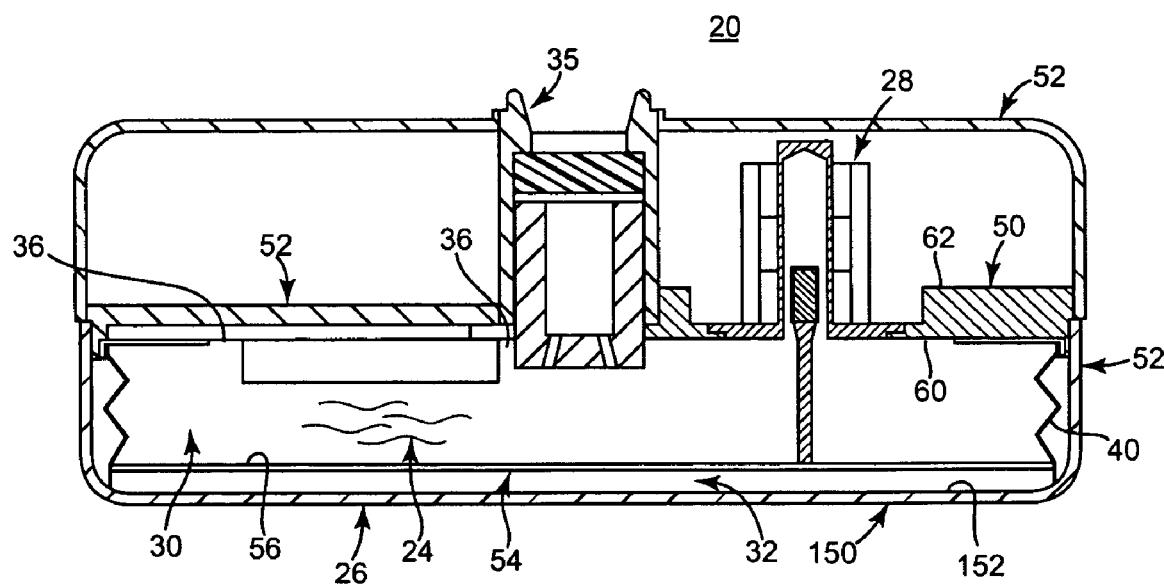
FIG. 2 is a simplified, cross-sectional view of the implantable therapeutic substance delivery device of FIG. 1A including a volume sensor assembly in accordance with principles of the present invention.

With the above background in mind, portions of one embodiment of the implantable therapeutic substance delivery device 20, including the volume sensor assembly 28, is generally illustrated in FIG. 2. Once again, the implantable therapeutic substance delivery device 20 includes the housing 26 forming the reservoir 30 (referenced generally) and maintaining the volume sensor assembly 28 (referenced generally). The reservoir 30 contains the implantable therapeutic substance 24 (drawn generally), and in some embodiments is acted upon by a propellant (not shown), such as an inert gas, contained within the propellant chamber 32 (e.g., where the reservoir 30 is defined in part by a bellows assembly 40).

The housing 26 includes a stationary wall 50 with which the volume sensor assembly 28 is associated. As a point of reference, the housing 26 can include a number of other walls (e.g., walls 52 as referenced generally in FIG. 2); however, the stationary wall 50 with which the volume sensor assembly 28 is associated with provides a consistent reference point relative to the reservoir 30. In some embodiments, the stationary wall 50 forms a part of the reservoir 30 (e.g., the stationary wall 50 is a bulkhead of the reservoir 30); in other embodiments the stationary wall 50 with which the volume sensor assembly 28 is associated with is provided apart from the reservoir 30. Regardless, the reservoir 30 is defined in part by a base wall 54 and includes the inlets and outlets 34, 36 (referenced generally) previously described, as well as an internal region 56 within which the therapeutic substance 24 is contained. In some embodiments, the base wall 54 is formed as part of the bellows assembly 40 that otherwise translates a positive pressure onto the contained therapeutic substance 24. Alternatively, the reservoir 30 can be defined in a variety of other forms. However, the base wall 54 is movable relative to the stationary wall 50 (and in particular an inner surface 60 thereof that is otherwise opposite an outer surface 62) such that the internal region 56 is variable. In other words, the reservoir 30 has a variable volume dictated by a position of the base wall 54 relative to the stationary wall 50.

In some embodiments, the base wall 54 is connected to the stationary wall 50 such that the internal region 56 increases in volume as the base wall 54 moves away from the stationary wall 50 (and decreases in volume as the base wall 54 moves towards the stationary wall 50). For example, in one embodiment, the propellant (not shown) within the propellant chamber 32 asserts a continuous, positive pressure onto the base wall 54, and thus onto the reservoir 30. Alternatively, and as previously described, the implantable therapeutic substance delivery device 20 can be configured such that a powered mechanism is coupled to the base wall 54 (or a corresponding component) that otherwise dictates a position of the base wall 54 relative to the stationary wall 50.

Figure 3A:
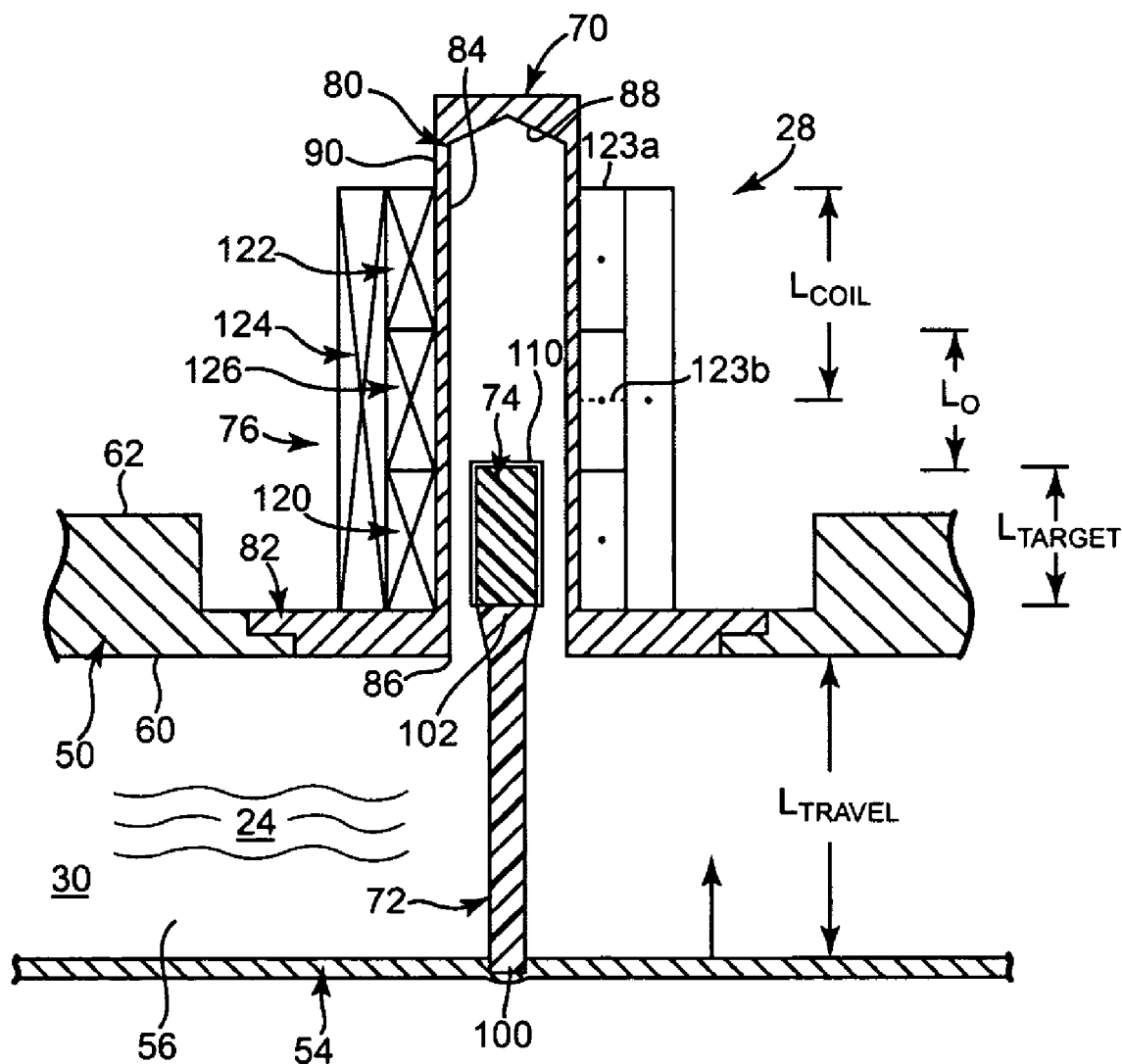
FIG. 3A is an enlarged view of a portion of the delivery device of FIG. 2, including the volume sensor assembly.

Regardless of an exact configuration, one embodiment of the volume sensor assembly 28 is shown in greater detail in FIG. 3A and includes a cap 70, a shaft 72, a target 74, and circuitry 76 (referenced generally). In general terms, the shaft 72 maintains the target 74 within the cap 70, with the circuitry 76 detecting a longitudinal position of the target 74 relative to the cap 70 and generating information indicative of this sensed position.

In one embodiment, the cap 70 includes a tubular member 80 and a flange 82. The tubular member 80 forms a passage 84 extending from a first, open end 86 to a second, closed end 88. Further, the tubular member 80 defines an exterior surface 90 approximating a length of the passage 84. The flange 82 is configured for sealed mounting to the stationary wall 50, extending in a generally radial fashion from the tubular member 80 at the open end 86. In one embodiment, the cap 70 is formed of a hardened, generally non-ferromagnetic material, for example titanium, capable of achieving a hermetic seal upon assembly to the stationary wall 50. In this regard, the cap 70 can be mounted to the stationary wall 50 in a wide variety of fashions. For example, in one embodiment, the flange 82 is welded to the stationary wall 50. Regardless, upon final assembly, the cap 70 is assembled to the stationary wall 50 such that the passage 84, and in particular the open end 86, is fluidly open relative to the inner surface 60 of the stationary wall 50. Thus, with the one embodiment of FIG. 3A in which the stationary wall 50 forms a portion of the reservoir 30, the passage 84 is fluidly open to the internal region 56. Regardless, the tubular member 80 extends away from the outer surface 62 of the stationary wall 50.

The shaft 72 defines a first end 100 and a second end 102. As described in greater detail below, a length of the shaft 72 corresponds with a maximum height of the reservoir 30 (e.g., a maximum length of travel of the base wall 54 relative to the stationary wall 50), and defines a maximum outer diameter less than the diameter of the passage 84 such that the shaft 72 is axially or longitudinally movable within the passage 84. Further, the shaft 72 is formed of a hardened and generally non-ferromagnetic material (e.g., titanium), that is otherwise compatible with the therapeutic substance 24 contained within the internal region 56. The first end 100 is configured for affixment to the base wall 54, such as by a laser welding operation. Conversely, the second end 102 is adapted to maintain the target 74 as described below.

In one embodiment, the target 74 is formed of a ferromagnetic material appropriate for magnetically inducing a current into the circuitry 76 as described below. The target 74 can assume a variety of sizes and shapes, but generally has a width sized to be smaller than a diameter of the passage 84. With this configuration, then, the target 74 is axially or longitudinally movable within the passage 84. As described in greater detail below, a length $L_{TARGET}$ of the target 74 corresponds with a length of certain components associated with the circuitry 76, as well as the length of travel $L_{TRAVEL}$ of the base wall 54 relative to the stationary wall 50. The target 74 is assembled to the second end 102 of the shaft 72 in a variety of fashions; for example, in one embodiment, the target 74 is welded to the second end 102 of the shaft 72. Further, to ensure compatibility with the contained therapeutic substance 24, in one embodiment, the volume sensor assembly 28 further includes an enclosure 110 surrounding the target 74. For example, the enclosure 110 can be a titanium body formed about the target 74 and sealed to the shaft 72 (e.g., via a laser weld process). With this configuration, the enclosure 110 ensures a compatible interface with the contained therapeutic substance 24. In alternative embodiments, for example where the volume sensor assembly 28 is configured such that the target 74 does not otherwise interface with the contained therapeutic substance 24, the enclosure 110 can be eliminated.

With the above construction, the target 74 is directly connected to the base wall 54 via the shaft 72, and thus moves with movement of the base wall 54. Conversely, the cap 70 is mounted to the stationary wall 50, and thus remains stationary with movement of the base wall 54/shaft 72. Thus, a known relationship is established between a longitudinal position of the target 74 relative to the passage 84 and a position of the stationary wall 50 relative to the base wall 54. Because a volume (or "current volume") of the reservoir 30 is defined as a function of a distance between the base wall 54 and the stationary wall 50, then, the longitudinal position of the target 74 relative to the passage 84 is a function of, or is indicative of, the current volume of the reservoir 30. With this in mind, the circuitry 76 is adapted to sense and/or provide information indicative of the position of the target 74 relative to the passage 84.

In one embodiment, the circuitry 76 includes first and second secondary wire coils 120, 122, and a primary wire coil 124, each of which are schematically illustrated in FIG. 3A. The first and second secondary coils 120, 122 are wound about the exterior surface 90 of the tubular member 80. Relative to the orientation of FIG. 3A, the first secondary wire coil 120 constitutes a lower coil, whereas the second secondary wire coil 122 constitutes an upper coil. Regardless, each of the secondary wire coils 120, 122 is formed of a material characterized as self-inducting in the presence of a magnetic body, for example the ferromagnetic target 74. Further, each of the secondary wire coils 120, 122 has a length $L_{COIL}$ (e.g., longitudinal distance between opposing, leading and trailing sides 123a, 123b identified for the second wire coil 122 in FIG. 3A) that is directly related to the length of travel $L_{TRAVEL}$ associated with the reservoir 30, and in particular of the base wall 54 relative to the stationary wall 50, and in turn relative to a length $L_{TARGET}$ of the target 74 as described in greater detail below. In one embodiment, however, first and second secondary wire coils 120, 122 are partially overlapped or co-axially wound relative to the lengths $L_{COIL}$ thereof. The overlapped region is indicated at 126 in FIG. 3A, and has a length $L_O$. For reasons made clear below, in one embodiment, a direction of winding of the first secondary wire coil 120 is opposite that of the second secondary wire coil 122. In other embodiments, the secondary wire coils 120, 122 are wound in the same direction. Regardless, each of the secondary wire coils 120, 122 are electrically connected to a sensing circuit or module (not shown, but can be provided as part of a controller or other circuitry otherwise conventionally provided with implantable drug pumps and/or external programmer) for measuring an output of the individual wire coils 120, 122.

The primary wire coil 124 is wound about an exterior of the secondary wire coils 120, 122. In one embodiment, the primary wire coil 124 extends a full length of the combined secondary wire coils 120, 122; in other embodiments, the primary wire coil 120 has a reduced length, for example sufficient to encompass only the overlapped region 126, etc. Preferably, the primary wire coil 124 is wrapped about at least a portion of each of the secondary wire coils 120, 122. With this arrangement, a mutual inductance relationship is created between the primary coil 124 and each of the secondary coils 120, 122 such that an electrical signal (or input signal) placed across the primary coil 124 is coupled into each of the secondary coils 120, 122. The amount of energy from the primary coil 124 actually inducted is enhanced by the presence of the ferromagnetic target 74. Thus, where the input signal is an alternating current defined by a sine wave, the resultant sine wave induced in the secondary coils 120, 122, and in particular the amplitude thereof, is increased via inductance caused by the ferromagnetic target 74.

In light of the above, the circuitry 76 is adapted to effectively measure a longitudinal position of the target 74 relative to the passage 84 based upon a comparison of the output signals from the secondary wire coils 120, 122. For example, the two output signals can be added to one another, with the resultant combined signal being indicative of a longitudinal position of the target 74. In the position of FIG. 3A, the target 74 is entirely within the first or lower coil 120. As a result, the first coil 120 output signal will be a large, in-phase sine wave. Conversely, the target 74 is fully displaced from the second or upper coil 122, resulting in a low output signal from the second coil 122. Appropriate comparison of the output signal can be performed in a variety of manners; for example in the one embodiment which the first coil 120 is wound in the same direction as the primary coil 124 and the second secondary coil 122 is wound in the opposite direction, the output signal from the second coil 122 will be 180° out of phase from that of the first coil 120. Thus, the secondary coil 120, 122 outputs can be directly added to one another. Alternatively, where the secondary coils 120, 122 are wound in the same direction, the output signal from the second coil 122 can be inverted prior to comparison with the first coil 120 output (or vice versa). Regardless, in the orientation of FIG. 3A, a comparison of the first and second secondary coil 120, 122 outputs results in a large, in-phase signal that is otherwise indicative of the target 74 being at the lower-most position shown. This, in turn, is indicative of the base wall 54 being spaced a maximum distance from the stationary wall 50, and thus of the reservoir 30 having a current volume approximating a maximum fill amount (or 100% full).

As the therapeutic substance 24 is dispensed from the reservoir 30, the base wall 54 moves relative to the stationary wall 50 (for example due to the positive pressure exerted thereon via the propellant chamber 32), shown by an arrow in FIG. 3A. As a result, the current volume of the reservoir 30, and thus the residual volume of the contained therapeutic substance 24, is reduced. Once again, the target 74 moves relative to the passage 84 via connection to the base wall 54 by the shaft 72, for example to the position shown in FIG. 3B. In this position, the target 74 is partially within both of the secondary wire coils 120, 122. As shown, however, a greater length of the target 74 is within the first secondary wire coil 120 as compared to the second secondary wire coil 122. Thus, the output signal from the first wire coil 120 has an increased amplitude as compared to the output signal from the second wire coil 122. When the output signals are compared, the combined signal is an in-phase sine wave (for embodiments in which the primary coil 124 and the first secondary coil 120 are wound in the same direction), with a decreased amplitude (as compared to that associated with the combined secondary coil 120, 122 outputs when the target 74 is in the lower-most position of FIG. 3A). Thus, as the target 74 travels from the lower-most position to a mid-point of travel, the combined output signal is an in-phase sine wave of decreasing amplitude. At the mid-point of travel, then, the first and second secondary wire coil 120, 122 outputs effectively cancel out. With further upward travel of the target 74, the output signal amplitude of the second coil 122 increases while that of the first coil 120 decreases. The combined output signal is a 180° out-of-phase sine wave, the amplitude of which increases as the target 74 travels from the mid-point to the top-most position shown in FIG. 3C. As a point of reference, the large, out-of-phase combined output signal resulting from the target 74 position of FIG. 3C corresponds with the base wall 54 having moved to a position commensurate with nearly complete depletion of the therapeutic substance 24 from the reservoir 30 such that the reservoir 30 is approximately 0% full (or empty).

The circuitry 76 output can be processed, manipulated and/or provided to a clinician in a wide variety of manners. For example, the combined output signal can simply be presented to and reviewed by the clinician, and a manual evaluation performed thereof to estimate a current volume of the reservoir 30 and thus a residual volume of the contained therapeutic substance 24. Alternatively, the circuitry 76 (or in other embodiments, circuitry associated with an external programmer) can be adapted to correlate and/or compare the combined output signal can be compared with a base line signal to estimate or indicate a fill percentage of the reservoir 30. For example, the combined output signal can be compared with the combined output signal generated when the target 74 is in the lower-most (and/or upper-most) position that is otherwise representative of the reservoir 30 being completely filled (or completely empty); based upon this comparison, an estimate can be made as to the current percent fill volume. In other embodiments, the combined output signal is compared with predetermined data points (e.g., a look-up table) that otherwise correlates signal information with volumetric values. For example, the amplitude and in-phase and out-of-phase components of the combined output signal can be compared with a table establishing a known relationship between the phase/amplitude values and corresponding volumes; or the reference table can equate fill percentage with combined output signal parameters.

Figure 3B:
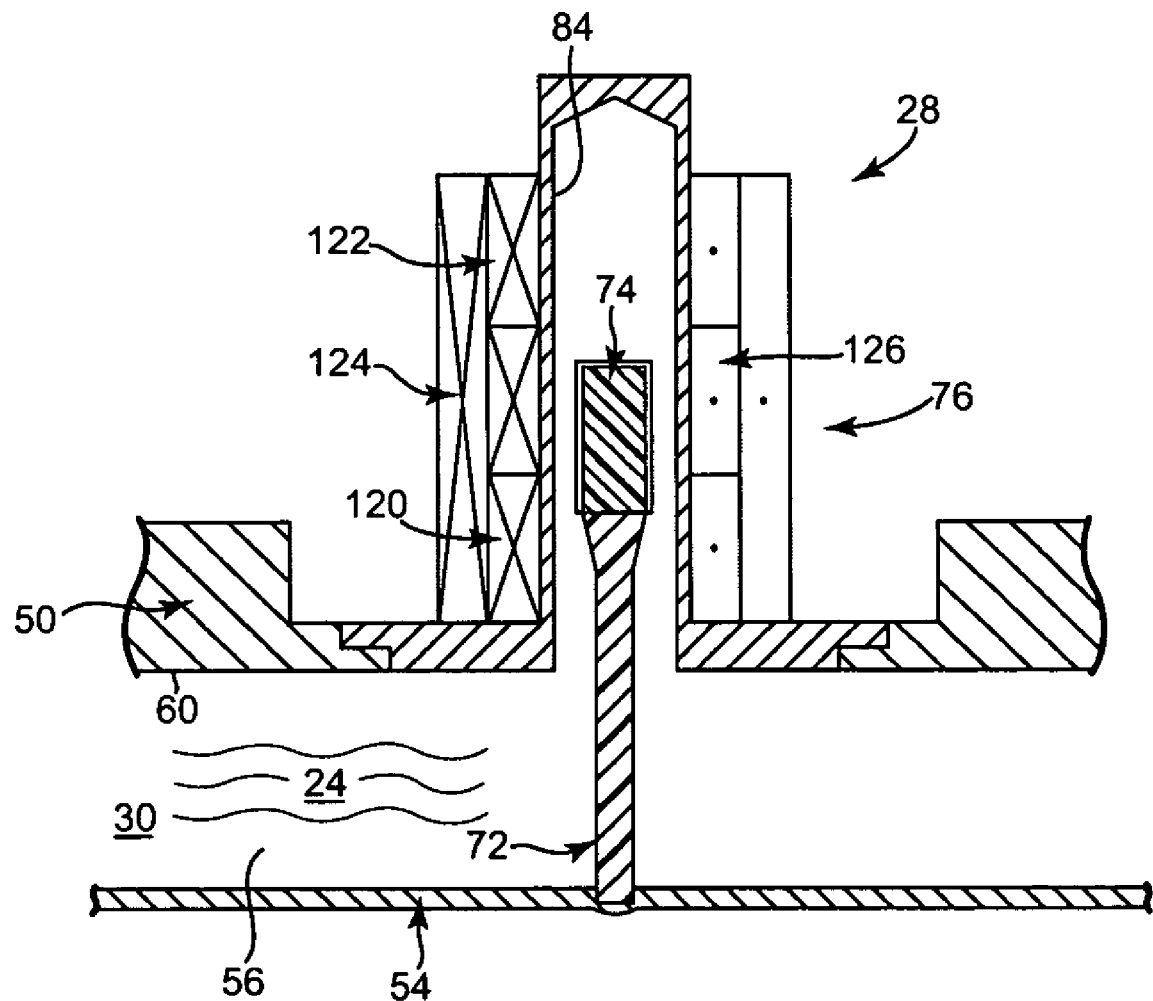
FIGS. 3B and 3C illustrate operation of the volume sensor assembly of FIG. 3A.
Figure 3C:
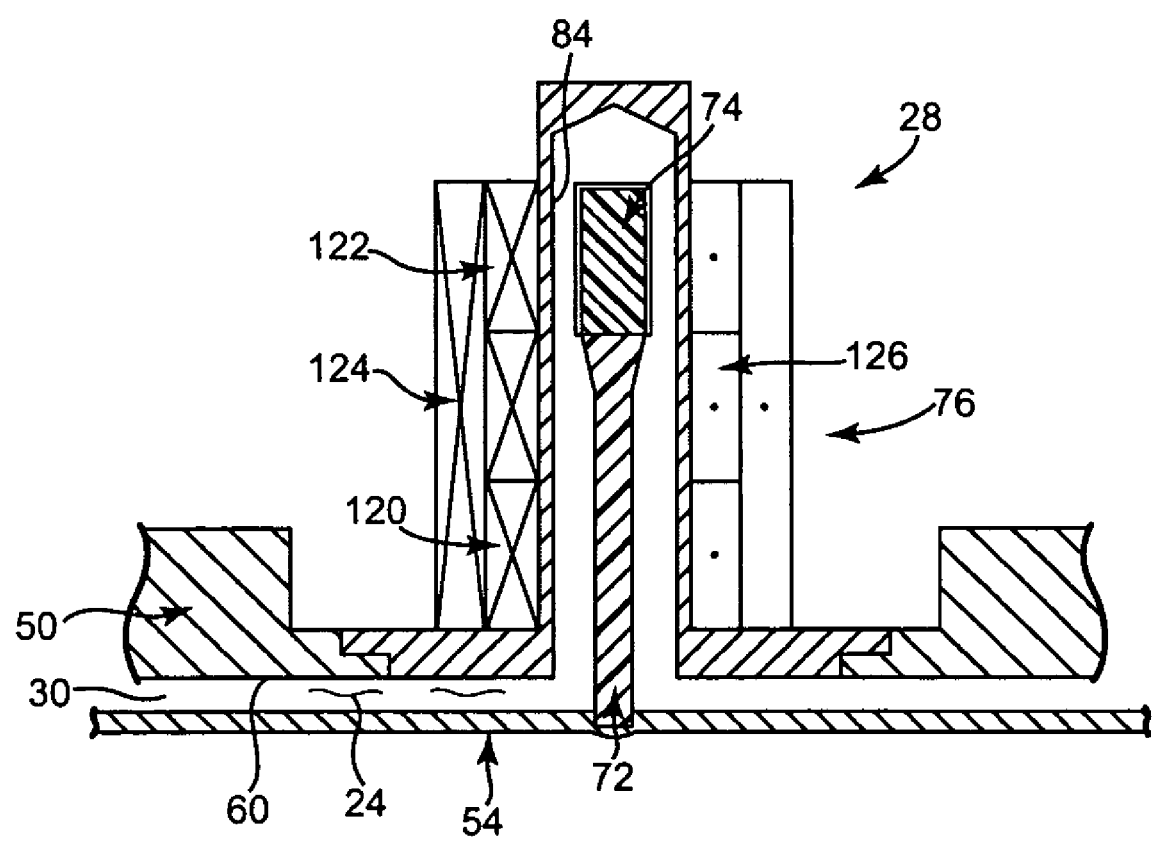

With the one embodiment of FIGS. 3A-3C, the volume sensor assembly 28 is adapted to generate an even and linear response in the secondary wire coils 120, 122 by correlating a size (e.g., length) of the target 74, passage 84, and the wire coils 120, 122, as well as the overlapped region 126. In particular, in one embodiment, the length $L_{TARGET}$ of the target 74 is approximately equal to one-half the length of travel $L_{TRAVEL}$ of the base wall 54 relative to the stationary wall 50. Further, the length $L_{COIL}$ of the first and second secondary coils 120, 122 is approximately 1.5×the length of travel $L_{TRAVEL}$, with the length $L_O$ of the overlapped region 126 approximating the length $L_{TARGET}$ of the target 74. Alternatively, other relationships can be employed, and in some embodiments, the length $L_{TARGET}$ of the target 74 is not directly related to the various other lengths. Along these same lines, more than two of the secondary wire coils 120, 122 can be provided (and their output signals compared). With additional secondary coils 120, 122, each individual, secondary coil can have a decreased length (as compared to that associated with the one embodiment of FIGS. 3A-3C in which two of the secondary wire coils 120, 122 are provided), as well as a reduction in overall length of the secondary coils, but would likely require a more complex demodulation of outputted signals. For example, a total length of the combined, partially overlapped, secondary coils associated with a three-secondary coil arrangement would approximately equal 1.3×length of travel $L_{TRAVEL}$ of the base wall 54 relative to the stationary wall 50, with the corresponding length $L_{TARGET}$ of the target 74 approximating one-third the length travel $L_{TRAVEL}$. Further, while the secondary wire coils 120, 122 are, in one embodiment, overlapped relative to one another, in other embodiments the secondary wire coils 120, 122 can be arranged side-by-side (i.e., with no overlap).

Figure 4:
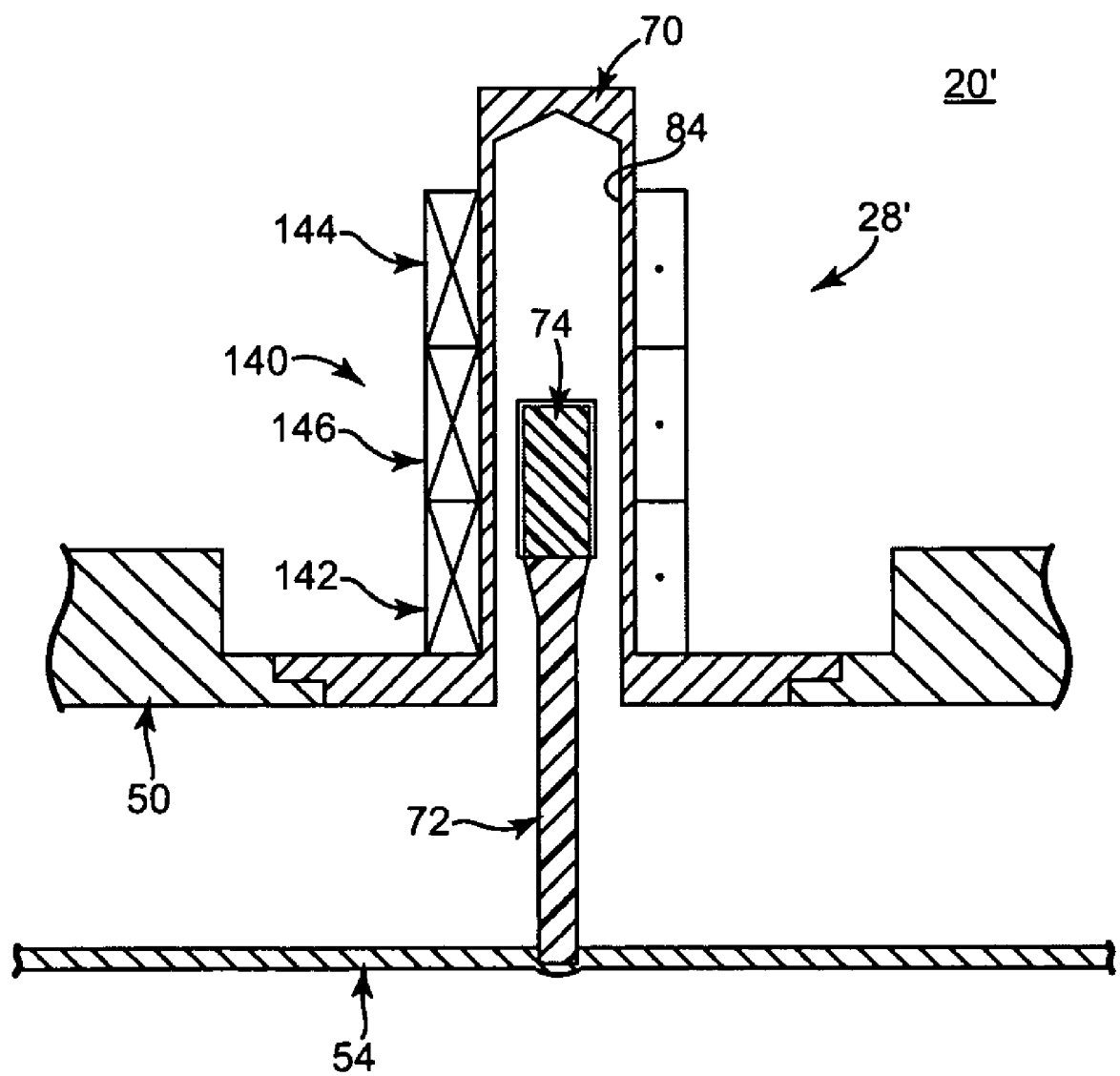
FIG. 4 is an enlarged cross-sectional view of another embodiment implantable therapeutic substance delivery device in accordance with principles of the present invention.

The circuitry 76 described above is but one example of an acceptable circuitry means in accordance with principles of the present invention. For example, FIG. 4 illustrates portions of an alternative embodiment implantable therapeutic substance delivery device 20' including an alternative embodiment volume sensor assembly 28'. In many respects, the device 20' is similar to the device 20 (FIGS. 3A-3C) previously described, with like elements being represented by like numbers. The volume sensor assembly 28' includes the cap 70, the shaft 72, and the target 74 as previously described, as well as circuitry 140 (referenced generally). In general terms, the circuitry 140 is adapted to generate information indicative of a longitudinal position of the target 74 relative to the passage 84 associated with the cap 70, based upon inductance created in the presence of the ferromagnetic target 74. In this regard, the circuitry 140 includes first and second wire coils 142, 144 that are otherwise similar to the wire coils 120, 122 (FIGS. 3A-3C) previously described. Unlike the circuitry 76 of FIGS. 3A-3C, however, the circuitry 140 does not include the primary coil 124. Instead, during use, the inductance of each of the wire coils 142, 144 is measured (through the use, for example, of an oscillator circuit (not shown)), with the measured inductances being used to indicate or estimate a position of the target 74 relative to the passage 84. For example, an inductance ratio can be established based upon the inductance $I_1$ of the first coil 142 and the inductance 12 of the second coil 144 as $I_1:I_2$. The inductance ratio $I_1:I_2$ can then be compared to predetermined data that otherwise correlates the inductance ratio $I_1:I_2$ with information indicative of the position of the target 74 relative to the passage 84. For example, the correlation information can be a curve representative of the relationship between the inductance ratio $I_1:I_2$ and the distance or displacement of the target 74 from the lower-most position (otherwise reflected in FIG. 4). A wide variety of other comparative relationships can also be employed.

As with previous embodiments, the configuration of FIG. 4 includes overlapping the first and second coils 142, 144 along approximately 50% of their respective lengths (represented by the overlap region 146 in FIG. 3). Further, the lengths of the target 74, the coils 142, 144, and the overlap region 146 are directly related to the length of travel of the base wall 54 relative to the stationary wall 50 as previously described. In alternative embodiments, however, more than two of the coils 142, 144 can be provided. Conversely, in other embodiments, a single wire coil is included that may or may not extend along an entirety of the expected length of travel of the target 74. In yet other embodiments, the coils 142, 144 are not overlapped.

While the previously described devices 20 (FIGS. 3A-3C), 20' have been described as employing a stationary wall (e.g., bulkhead) of the reservoir 30 as the stationary wall 50 reference point relative to movement of the base wall 54, in other embodiments, the volume sensor assembly 28 (FIGS. 3A-3C), 28' can be associated employ a different stationary body. For example, with reference to FIGS. 2 and 3A, the cap 70 can instead be assembled to a stationary wall 150 (FIG. 2) of the housing 26 that does not otherwise define a face of the reservoir 30. More particularly, the identified wall 150 forms a portion of the housing 26 apart from the reservoir 30, and includes a face 152 (FIG. 2) that remains stationary with movement of the base wall 54. With this embodiment, then, the cap 70 is assembled to the reservoir wall 150 such that the passage 84 is open relative to an inner face 154 thereof. The shaft 72 is assembled to the base wall 54, and extends toward the wall 150 such that the target 74 is movably positioned within the passage 84. With this configuration, the target 74 moves relative to the passage 84 with movement of the base wall 54 relative to the reservoir wall 150. In contrast to previous embodiments, with this alternative configuration, the target 74 is proximate the closed end 88 of the passage 84 when the reservoir 30 is full (i.e., when the base wall 54 has reached a minimum spacing relative to the reservoir wall 150). All remaining aspects of the volume sensor assemblies 28, 28' previously described remain unchanged.

While the secondary wire coils 120, 122 have been described as encompassing an entire length of travel of the target 74 relative to the passage 84, in alternative embodiments, less complete coverage is provided. For example, it may be preferred that residual volume information is generated only as the reservoir 30 approaches a depleted state. With this in mind, the volume sensor assembly 28 (FIGS. 3A-3C), 28' (FIG. 4) can alternatively be configured to generate information indicative of the base wall 54 position, and thus of the reservoir 30 volume, under circumstances where the reservoir 30 and/or residual volume of the contained therapeutic substance 24 is less than 100% full. Thus, for example, the volume sensor assemblies 28, 28' can be configured to generate information indicative of reservoir 30 volume once the volume has been reduced to 50% or less than full.

Regardless of an exact form of the volume sensor assembly 28, 28', the volume-related information can be conveyed to the clinician in a variety of manners. In one embodiment, and returning to FIG. 1B, the device 20 further includes an enunciation device 160 configured to generate an audible noise, for example an audible tone. The enunciation device 160 can be maintained by the housing 26; in alternative embodiments, the enunciation device 160 is provided apart from the device 20 (such as part of a remote programmer (not shown)).

Regardless, the enunciation device 160 is electronically coupled to the volume sensor assembly 28, such as via a controller 162. The controller 162 may be provided as part of the enunciation device 160, as part of a separate control circuitry otherwise controlling operations of the device 20, or external from the housing 26 (such as part of a remote programmer). Regardless, the controller 162 receives information from the volume sensor assembly 28 indicative of a current volume of the reservoir 30, and thus of a residual volume of the therapeutic substance 24 contained within the reservoir 30, and based upon this information, prompts operation of the enunciation device 160 in a manner otherwise indicative of the residual volume. For example, in one embodiment, the enunciation device 160 generates an on-and-off tone in accordance with a selected duty cycle. With this in mind, the controller 162 is adapted or programmed to control the duty cycle of the on-and-off tone to be proportional to the current volume status of the reservoir 30. For example, when the volume sensor assembly 28 provides information indicative of the reservoir 30 being approximately empty, the sequence issued by the enunciation device 160 is controlled to be a very short tone length followed by a long silent period, and repeated. During a filling process, as the reservoir 30 is filled, the controller 162 prompts the enunciation device 160 to generate a longer "on" tone, and a shorter silent period, such that the total period of the cycle is constant. This proportional relationship continues until the volume sensor assembly 28 indicate that the reservoir 30 is full, at which point the enunciation device 160 issues a steady, uninterrupted tone.

The above enunciation/tone sequence is but one format in accordance with the principles of the present invention. Thus, a different tone sequence format can be employed. In fact, in other embodiments, the enunciation device 160 is eliminated. Conversely, the above-described enunciation device 160 and the controlled tone sequence associated therewith can be employed with an implantable therapeutic substance delivery device employing an entirely different volume sensor assembly. In one embodiment, however, the above-described tone sequence format can be initiated upon determining that a clinician desires to perform a filling process, such as via a needle detector associated with the fill port 35 (FIG. 2) otherwise fluidly connected to the reservoir 30 as is known in the art. With this technique, when the controller 162 is alerted (e.g., via telemetry) that a fill sequence is about to occur, the controller 162 polls for a signal from the needle detector. Once the needle detector indicates that the filling needle is within the fill port 35, the tone sequence is initiated by the controller 162. Further, the controller 162 can terminate the tone sequence any time the needle sensor indicates that the filling needle has been removed from the fill port. Alternatively, the controller 162 can be remotely prompted by the clinician to initiate operation of the enunciation device 160.

The implantable therapeutic substance delivery device and associated volume sensor assembly of the present invention provides a marked improvement over previous designs. Information indicative of a current volume of the drug reservoir, and thus of the residual volume of the contained therapeutic substance, is determined directly from the reservoir itself, as opposed to relying upon calculations that assume consistent delivery of expected volumes from the device. Also, the accuracy of the volume sensor assembly is not degraded by the nature of the contained therapeutic substance or by an orientation of the device. Further, the volume sensor assembly does not place any materials in contact with the contained therapeutic substance that would be chemically or otherwise incompatible with the media. Additionally, the volume sensor assembly does not entail passing of an electrical signal across a sealed barrier, and thus does not require an electrical feedthru into an otherwise sealed chamber.

Although the present invention has been described with reference to preferred embodiments, workers skilled in the art will recognize that changes can be made in form and detail without departing from the spirit and scope of the present invention. For example, while the volume sensor assembly has been described as including a shaft slidably maintaining a ferromagnetic target within a passage otherwise exteriorly surrounded by one or more wire coils, other volume sensing means are also contemplated. For example, a position of the target relative to the passage can be sensed or determined using other circuitry arrangements, such as electronic switch(es), mechanicals actuator(s), etc. Similarly, movement and/or spatial positioning of a moveable wall of the drug reservoir can be sensed or determined using configurations that do not necessarily include a shaft and/or a ferromagnetic target.

What is claimed is:

1. An implantable medical device for delivering a liquid therapeutic substance to a delivery site within a patient, the device comprising:
    a housing including a stationary wall, having an inner face and an outer face, and maintaining a reservoir defining an internal region for containing the therapeutic substance, the reservoir including:
        an inlet,
        an outlet,
        a base wall that is movable relative to the stationary wall, wherein a volume of the internal region is a function of a distance between the base wall and the stationary wall; and
    a volume sensor assembly for generating information indicative of a current volume of the internal region, the assembly including:
        a cap defining an internal passage extending from an open end to a closed end, the cap being mounted to the stationary wall such that the open end of the passage is open relative to the inner face and the internal region of the reservoir,
        a shaft comprised of a non-ferromagnetic material having a first end and a second end, wherein the first end is attached to the base wall opposite the cap,
        a target comprised of a ferromagnetic material assembled to the second end of the shaft and movably arranged within the passage,
        circuitry associated with the cap and adapted to detect a longitudinal position of the target within the passage and generate information indicative of the longitudinal position of the target relative to a dimension of the cap;
    wherein the longitudinal position of the target relative to the dimension of the cap is representative of the volume of the internal region.

2. The device of claim 1, wherein the volume of the internal region changes with movement of the base wall relative to the stationary wall, and the target moves relative to the cap with movement of the base wall via the shaft, and further wherein the volume sensor assembly is configured to establish a linear relationship between movement of the base wall and movement of the target.

3. The device of claim 2, wherein the reservoir is configured such that at a first position of the base wall relative to the stationary wall, the internal region has a maximum volume and at a second position of the base wall relative to the stationary wall, the internal region has a minimum volume, with the base wall defining a length of travel in transitioning from the first position to the second position, and further wherein the passage has a length corresponding with the length of travel.

4. The device of claim 1, wherein the reservoir is configured such that the internal region has a variable volume, ranging from 100% full to 0% full, and further wherein the volume sensor assembly is adapted to generate information indicative of a current volume at least over the range of approximately 0% full-50% full.

5. The device of claim 1, wherein the volume sensor assembly is adapted to indicate a fill percentage of the internal region.

6. The device of claim 1, wherein the volume sensor assembly is adapted to indicate a residual volume of the therapeutic substance contained by the internal region.

7. The device of claim 1, wherein the cap includes a tubular member defining the passage and having an exterior surface and a flange extending radially from the tubular member at the open end, and further wherein the circuitry includes:
   a first wire coil disposed about the exterior surface along a portion of the length thereof; and
   a sensing device for sensing information relating to inductance of the first wire coil.

8. The device of claim 7, wherein the circuitry further includes a second wire coil disposed about the exterior surface of the tubular member along a length thereof and wound in a direction opposite that of the first coil wire, the sensing device being further adapted to sense information relating to inductance of the second wire coil.

9. The device of claim 8, wherein each of the wire coils defines a length between a leading side and a trailing side, and further wherein the wire coils are assembled to the tubular member such that a portion of the length of the first wire coil overlaps a portion of a length of the second wire coil.

10. The device of claim 9, wherein the base wall is movable between a first position relative to the stationary wall corresponding with a first volume of the internal region and a second position relative to the stationary wall corresponding with a second volume of the internal region, the first volume being greater than the second volume and a distance from the first position to the second position defining a length of travel, and further wherein a length of each of the wire coils is related to the length of travel.

11. The device of claim 10, wherein the first position corresponds with a maximum volume of the reservoir and the second position corresponds with a minimum volume of the reservoir.

12. The device of claim 10, wherein the length of each of the wire coils approximately equals the length of travel.

13. The device of claim 12, wherein the wire coils overlap one another along approximately 50% of their corresponding lengths.

14. The device of claim 8, wherein the sensing device is adapted to monitor an inductance of the first and second wire coils.

15. The device of claim 14, wherein the sensing device is further adapted to compare the monitored inductance of the first and second wire coils.

16. The device of claim 8, wherein the circuitry further includes a third wire coil wound about at least a portion of the first and second wire coils.

17. The device of claim 16, wherein the circuitry further includes a generator electrically connected to the third wire coil and adapted to generate a sinusoidal current through the third wire coil, and further wherein the sensing device is adapted to sense and compare wave signals generated by the first and second wire coils.

18. The device of claim 7, wherein the target defines a length in a direction parallel with a central axis of the passage, and further wherein the length of the target corresponds with a length of the first wire coil.

19. The device of claim 18, wherein the circuitry further includes a second wire coil disposed about the tubular member and partially overlapping the first wire coil, and further wherein the length of the target corresponds with a length of overlap of the first and second wire coils.

20. The device of claim 1, wherein the volume sensor assembly further includes an enclosure surrounding the ferromagnetic material, the enclosure being formed of a material compatible with the therapeutic substance.

21. The device of claim 1, wherein the stationary wall defines a wall of the reservoir opposite the base wall.

22. The device of claim 21, wherein the stationary wall is a bulkhead.

23. The device of claim 1, wherein the base wall is provided as part of a bellows assembly.

24. The device of claim 1, further comprising:
   an enunciation device maintained by the housing; and
   a controller electronically connected to the volume sensor assembly and the enunciation device, the controller adapted to:
      receive the information indicative of current volume from the volume sensor assembly, and
      prompt operation of the enunciation device based upon the received information.

25. The device of claim 24, wherein the enunciation device is adapted to produce audible tones of varying length, and wherein the controller is further adapted to prompt operation of the enunciation device such that at least one of a length of individual tones and a time period between successive tones is indicative of the current volume of the therapeutic substance contained in the reservoir.

26. The device of claim 25, wherein the controller is further adapted to prompt the enunciation device to produce tones having an increasingly longer length as the volume sensor assembly indicates that a volume of the contained therapeutic substance is increasing.

27. A method of operating an implantable medical device adapted to deliver a liquid therapeutic substance, otherwise contained within a drug reservoir of the implantable medical device, to a delivery site within a patient following implantation of the implantable medical device, the method comprising:
   operating a volume sensor assembly associated with the reservoir to obtain target position information, the assembly including:
      a cap defining an internal passage extending from an open end to a closed end, the cap being mounted relative to the reservoir such that the open end of the passage faces a movable, base wall of the reservoir,
      a shaft having a first end and a second end, wherein the first end is attached to the base wall opposite the cap,
      a target assembled to the second end of the shaft and movably arranged within the passage, wherein the target defines a length in a direction parallel with a central axis of the passage,
      circuitry associated with the cap and adapted to generate information indicative of a longitudinal position of the target relative to a dimension of the cap, the circuitry including a wire coil disposed on an exterior surface of the cap,
      wherein the length of the target corresponds with a length of the wire coil in a direction parallel with the central axis of the passage;

processing the obtained target position information to generate information indicative of a current volume of the reservoir;

wherein the information indicative of the current volume is obtained without passing an electrical signal across the reservoir; and determining whether to add therapeutic material to the reservoir based upon the generated current volume information.

28. The method of claim 27, wherein the volume sensor assembly includes a plurality of wire coils, and further wherein operating the volume sensor assembly to obtain target position information includes:

sensing inductance information for at least two of the wire coils.

29. The method of claim 28, wherein generating information indicative of the current volume includes:

comparing the inductance information; and generating a relative fill volume value based upon the comparison.

30. The method of claim 27, further comprising:

operating an enunciation device to produce a series of audible tones as a function of the current volume information.

31. An implantable medical device for delivering a therapeutic substance to a delivery site within a patient, the device comprising:

a housing including a stationary wall and maintaining a drug reservoir defining an internal region for containing the therapeutic substance, the drug reservoir including:

an inlet, an outlet, a base wall that is movable relative to the stationary wall, wherein a volume of the internal region is a function of a distance between the base wall and the stationary wall, volume sensing means for generating information indicative of a current volume of the internal region, the volume sensing means including:

a target means connected to the base wall and slidably disposed within a cap, circuitry means for generating information indicative of a longitudinal position of the target means relative to the cap, the circuitry means including a first wire coil wound about the cap and a second wire coil overlapping only a portion of the first wire coil, the wire coils being electrically affected by the target.

32. The device of claim 31, wherein the circuitry means is adapted to signal information indicative of an inductance of at least one of the wire coils.

33. An implantable medical device for delivering a liquid therapeutic substance to a delivery site within a patient, the device comprising:

a housing including a stationary wall, having an inner face and an outer face, and maintaining a reservoir defining an internal region for containing the therapeutic substance, the reservoir including:

an inlet, an outlet, a base wall that is movable relative to the stationary wall, wherein a volume of the internal region is a function of a distance between the base wall and the stationary wall; and a volume sensor assembly for generating information indicative of a current volume of the internal region, the assembly including:

a cap including a tubular member defining an exterior surface and an internal passage extending from an open end to a closed end, the cap being mounted to the stationary wall such that the open end of the passage is open relative to the inner face, a shaft disposed within the internal region of the reservoir and having a first end and a second end, wherein the first end is attached to the base wall opposite the cap, a target maintained by the second end of the shaft and movably arranged within the passage, circuitry associated with the cap and adapted to generate information indicative of a longitudinal position of the target relative to a dimension of the cap, the circuitry including a primary wire coil and a secondary wire coil disposed about the exterior surface along a portion of a length of the tubular member;

wherein the longitudinal position of the target relative to the dimension of the cap is representative of the volume of the internal region.

* * * * *